United States Patent [19]

Mainster et al.

[11] Patent Number: 5,589,896
[45] Date of Patent: Dec. 31, 1996

[54] ADJUSTABLE INDIRECT OPHTHALMOSCOPY LENS

[75] Inventors: Martin A. Mainster, Leawood, Kans.; Janet L. Crossman; Robert D. Johnson, both of Bellevue, Wash.

[73] Assignee: Ocular Instruments, Inc., Bellevue, Wash.

[21] Appl. No.: 329,711

[22] Filed: Oct. 26, 1994

[51] Int. Cl.⁶ .............................. A61B 3/00; A61B 3/10; G02B 15/14

[52] U.S. Cl. ...................... 351/219; 351/205; 359/689; 359/708

[58] Field of Search ................................. 351/200, 205, 351/206, 219, 160 R; 354/62; 359/689, 686, 691, 708

[56] References Cited

U.S. PATENT DOCUMENTS

| | | | |
|---|---|---|---|
| 3,770,342 | 11/1973 | Dudragne | 351/7 |
| 3,820,879 | 6/1974 | Frisen | 351/1 |
| 3,954,329 | 5/1976 | Pomerantzeff | 351/16 |
| 4,023,189 | 5/1977 | Govignon | 354/62 |
| 4,027,952 | 6/1977 | Hugues | 350/189 |
| 4,134,647 | 6/1979 | Ramos-Caldera | 351/6 |
| 4,222,634 | 9/1980 | Muchel | 350/189 |
| 4,265,519 | 5/1981 | Pomerantzeff | 351/16 |
| 4,357,088 | 11/1982 | Pomerantzeff | 354/62 |
| 4,410,245 | 1/1983 | Koester | 351/219 |
| 4,452,514 | 6/1984 | Spitznas | 351/206 |
| 4,469,413 | 9/1984 | Shirayanagi | 350/432 |
| 4,502,764 | 3/1985 | Riquin | 351/160 R |
| 4,627,694 | 12/1986 | Volk | 351/214 |
| 4,637,699 | 1/1987 | Sigelman | 351/205 |
| 4,669,839 | 6/1987 | Muchel | 351/221 |
| 4,671,631 | 6/1987 | Sigelman | 351/205 |
| 4,682,866 | 7/1987 | Volk | 351/205 |
| 4,704,018 | 11/1987 | Takahashi | 351/206 |
| 4,721,378 | 1/1988 | Volk | 351/205 |
| 4,728,183 | 3/1988 | Heacock et al. | 351/219 |
| 4,738,521 | 4/1988 | Volk | 351/205 |
| 4,801,198 | 1/1989 | Heacock et al. | 351/214 |
| 5,007,729 | 4/1991 | Erickson et al. | 351/219 |
| 5,189,450 | 2/1993 | Crossman et al. | 351/219 |
| 5,309,187 | 5/1994 | Crossman et al. | 351/219 |
| 5,430,506 | 7/1995 | Volk | 351/205 |

FOREIGN PATENT DOCUMENTS

| | | | |
|---|---|---|---|
| 2136927 | 12/1972 | France . | |
| 2248814 | 5/1975 | France | 351/219 |
| 1188326 | 3/1965 | Germany . | |
| 2246182 | 3/1974 | Germany | 351/219 |
| 2660505C2 | 9/1977 | Germany | 351/219 |
| 2610821 | 12/1977 | Germany . | |
| 2559668 | 5/1979 | Germany . | |
| 2203260 | 10/1988 | United Kingdom . | |
| WO84/01703 | 5/1984 | WIPO . | |

OTHER PUBLICATIONS

Sudarsky, R. D., Volk, D., "Aspherical Objective Lenses as Aid in Indirect Ophthalmoscopy, A Preliminary Report," Reprinted from *American Journal of Ophthalmology* 47:572–575 (Apr. 1959).

James H. Allen, M. D., *May's Manual of the Diseases of the Eye for Students and General Practitioners*, 24th ed., The Williams & Wilkins Company, Baltimore, 1968, p. 280 (No Month).

Schlegel, H. J., "Simple Wide–Angle Optics for Split Lamp Microscopy Examinations of the Fundus of the Eye (Panfundoscopy)," *Documenta Ophthalmologica* 26:300–308 (1969)(No Month).

Sir Stewart Duke–Elder and David Abrams, *System of Ophthalmology, vol. 5, Ophthalmic Optics and Refraction*, The C. V. Mosby Company, St. Louis, 1970, p. 423 (No Month).

(List continued on next page.)

*Primary Examiner*—Huy Mai
*Attorney, Agent, or Firm*—Christensen, O'Connor, Johnson & Kindness, P.L.L.C.

[57] ABSTRACT

An indirect ophthalmoscopy lens (10) comprises two or more elements (16, 30). The elements (16, 30) are movable by the physician relative to each other to vary the magnification provided in an aerial image (I) of the fundus.

4 Claims, 5 Drawing Sheets

OTHER PUBLICATIONS

Pomerantzeff, O., Govignon, J., "Design of a Wide–Angle Ophthalmoscope," *Arch. Opthal.* 86:420–424 (Oct. 1971).

Pomerantzeff, O., "A Lens System for Wide–Angle Fundus Photography," *Ophthalmic Photography* 16:101–108 (Summer 1976)(No Month).

Pomerantzeff, O., "Theory and Practice of the Equator Plus Camera (EPC)", Conf. Proceedings of International Symposium on Ophthalmological Optics (May 7–9, 1978) 117–118.

Pomerantzeff, O., Webb, R. H., Delori, F. C., "Image Formation in Fundus Cameras," *Invest. Ophthalmol. Visual Sci.* 18:630–637 (Jun. 1979).

Pomerantzeff, O., "Wide–Angle Noncontact and Small–Angle Contact Cameras," *Invest. Ophthalmol. Visual Sci.* 19:973–979 (Aug. 1980).

Charles, L. Schepens, M. D., *Retinal Detachment and Allied Diseases,* W. B. Saunders Company, Philadelphia, 1983, Ch. 43, "New and Improved Diagnostic and Surgical Procedures," pp. 1107–1155 (No Month).

P. Roussel et al, "Contact Glass for Use . . . Optical Aspects," *International Ophthalmology* 6:183–190 (1983) (No Month).

Dieckert, J. P. et al., "Contact Lenses for Laser Applications," *Ophthalmology: Instrument and Book Supplement* 79–87 (1984) (No Month).

Arnold Sorsby, Ch. 34, "Biology of the Eye as an Optical System," pp. 1–17 (No date).

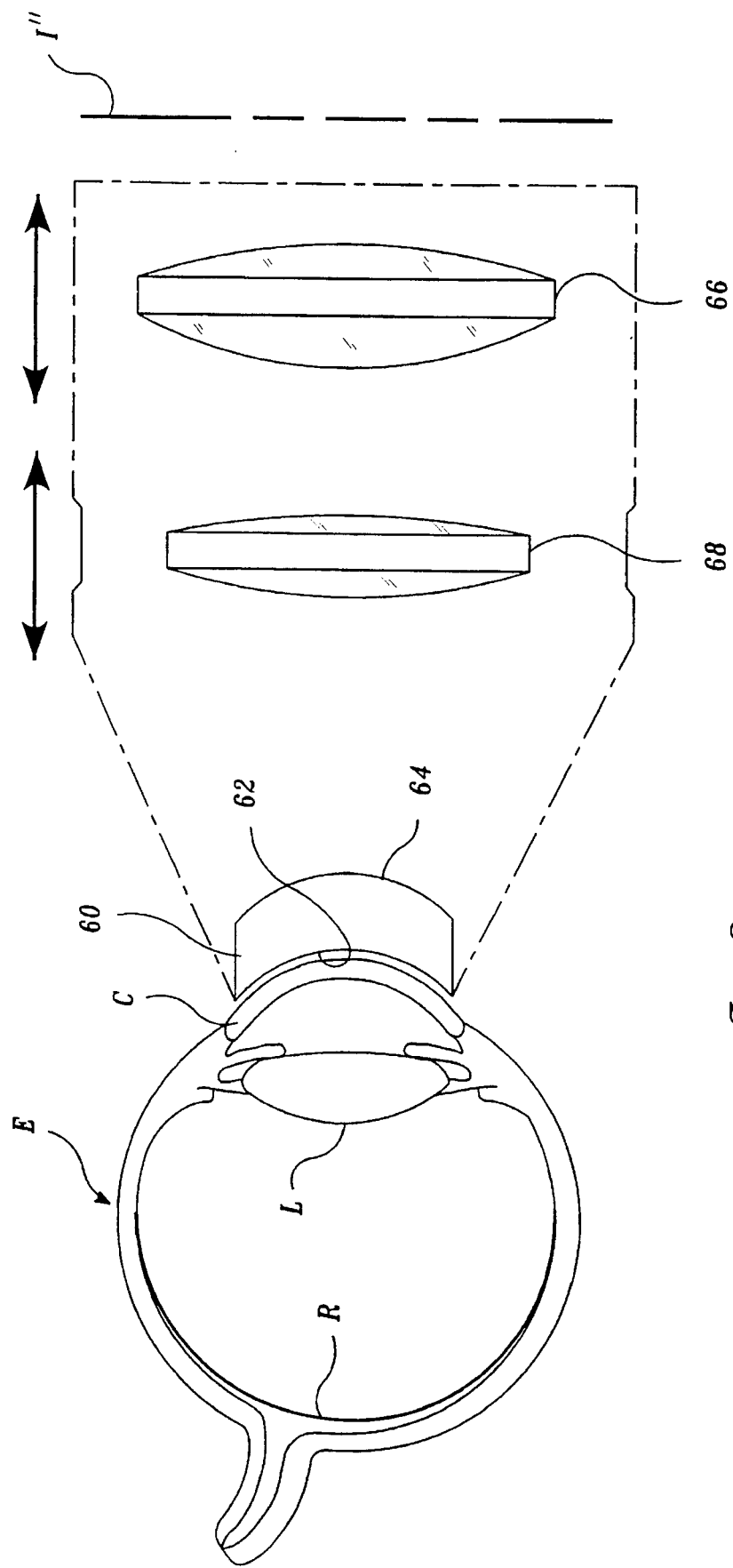

5,589,896

ADJUSTABLE INDIRECT OPHTHALMOSCOPY LENS

FIELD OF THE INVENTION

The present invention relates to ophthalmoscopy lenses, and more particularly to an adjustable ophthalmoscopy lens useful in examination and treatment of various portions of the eye.

BACKGROUND OF THE INVENTION

Ophthalmologists employ both contact and noncontact indirect ophthalmoscopy lenses for viewing the fundus of the eye. These lenses, which provide an aerial image of the fundus anterior to the lens, are used for both diagnosis and for subsequent laser treatment where indicated. Typically, an ophthalmologist prefers to first use a low magnification wide field lens in order to obtain an overview of the patient's fundus. The ophthalmologist then switches to a higher magnification lens in order to examine a specific area of interest in greater detail. Switching of lenses is time-consuming and cumbersome, especially in the case of contact lenses. Also, physicians with heavy patient schedules and multiple examination rooms encounter difficulty in tracking the whereabouts of various lenses of different power.

Rather than switching lenses to magnify the image of the fundus, the variable magnification capabilities of the slit lamp or indirect ophthalmoscope are used by the physician to magnify the fundus image. While this provides greater magnification for the ophthalmologist, it provides little or no increase in the amount of information or fundus detail available to the physician.

SUMMARY OF THE INVENTION

The present invention provides a novel and greatly improved indirect ophthalmoscopy lens which provides the ophthalmologist with the capability of varying the magnification of an indirect ophthalmoscopy lens without changing lenses and without changing the variable adjustable magnification of the microscope. The lens of the present invention includes a posterior lens and an anterior lens. The posterior lens has a posterior surface having a predetermined curvature and being adapted to be placed in juxtaposition to the cornea. The posterior lens also has an anterior surface with a predetermined curvature. The anterior lens has a posterior surface and an anterior surface, both having curvatures adapted to focus light rays emanating from the fundus and passing through the posterior lens when the latter is in juxtaposition to the cornea. The light rays are focused in an aerial image anterior to and in close proximity to the anterior surface of the anterior lens. In accordance with the present invention, means are provided for coupling the posterior lens and the anterior lens together so that the anterior lens and the posterior lens are substantially coincident along their optical axes. The coupling means also allow the anterior lens to be moved axially relative to the posterior lens between a position proximal to the posterior lens and a position distal from the posterior lens. The surfaces of the posterior lens and the surfaces of the anterior lens cooperate to change the magnification of the aerial image from at least a first predetermined value when the anterior lens is in a proximal position to a second predetermined value when the anterior lens is in a distal position. The coupling means can be manipulated by a free finger of the ophthalmologist as he holds the posterior lens in juxtaposition to the eye. By manipulating the coupling means, the ophthalmologist can change the aerial image from a wide field, lower magnification to a higher magnification, slightly narrower field. When the lens is changed to a higher magnification, more retinal detail is provided. This additional detail is beneficial in determining the amount or boundaries of retinal thickening, for example. Also, other stereoscopic details are enhanced such as macular edema or optic disc cupping.

In addition to the diagnostic advantages, laser treatment of more than one type can now be performed with a single device. For example, a panretinal photocoagulation requires a wide field of view but little or no stereoscopic detail. At the completion of the panretinal photocoagulation, the physician may wish to perform a focal laser treatment. In that case, stereoscopic detail is desirable and can be provided by the lens of the present invention by simply manipulating the coupling means to increase the magnification. Thus, the lens of the present invention eliminates the need to change to another fixed magnification lens and allows the physician to much more efficiently and economically diagnose and treat the patient.

BRIEF DESCRIPTION OF THE DRAWINGS

A better understanding of the present invention can be derived by reading the ensuing specification in conjunction with the accompanying drawings wherein:

FIG. 3 is a schematic view of an indirect ophthalmoscopy lens of the contact type having a corneal contact lens, an intermediate lens, and an anterior lens.

DETAILED DESCRIPTION OF THE PREFERRED EMBODIMENT

Figure 1:
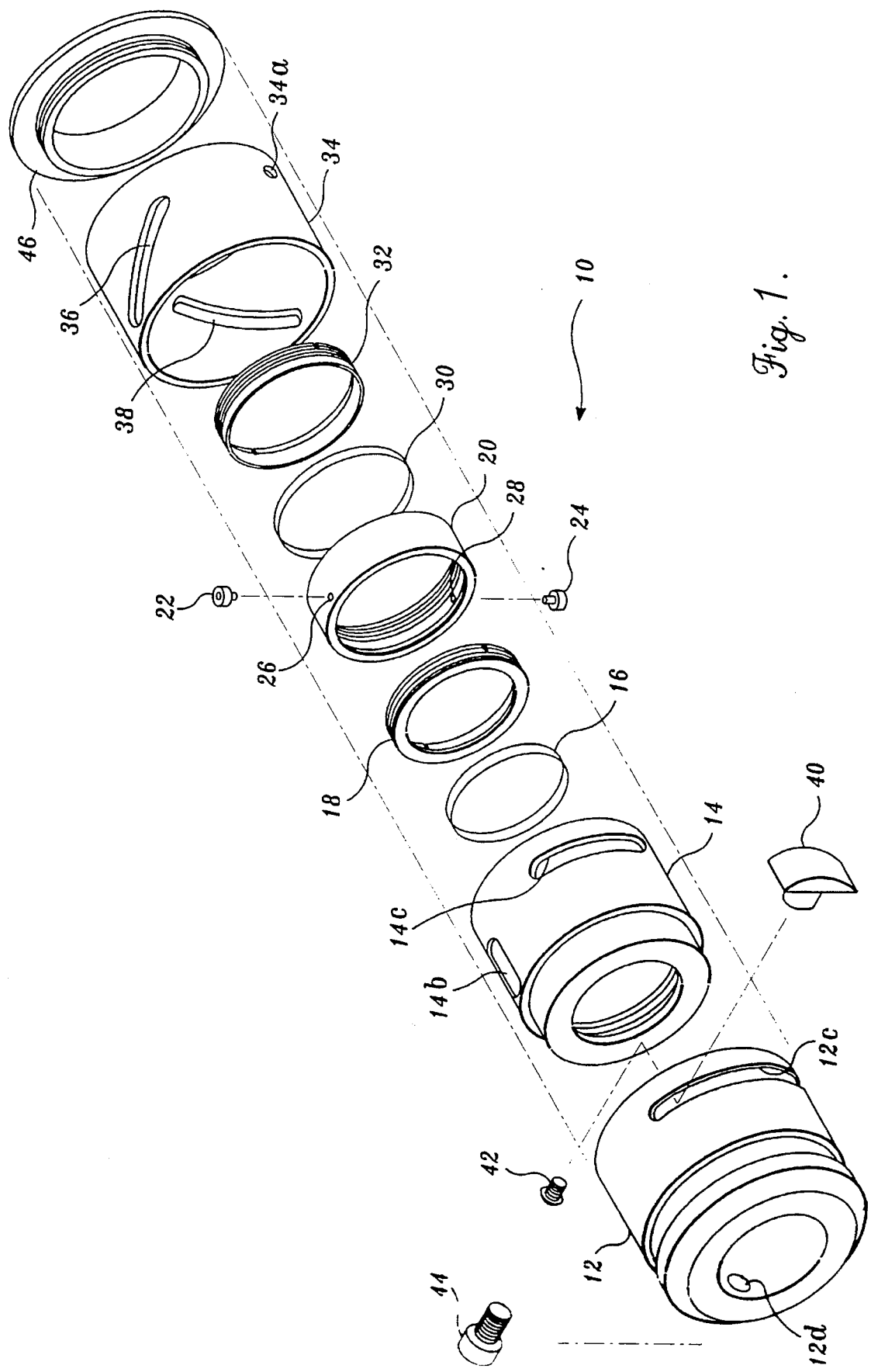
FIG. 1 is an exploded isometric view of the ophthalmoscopy lens constructed in accordance with the present invention.
Figure 2A:
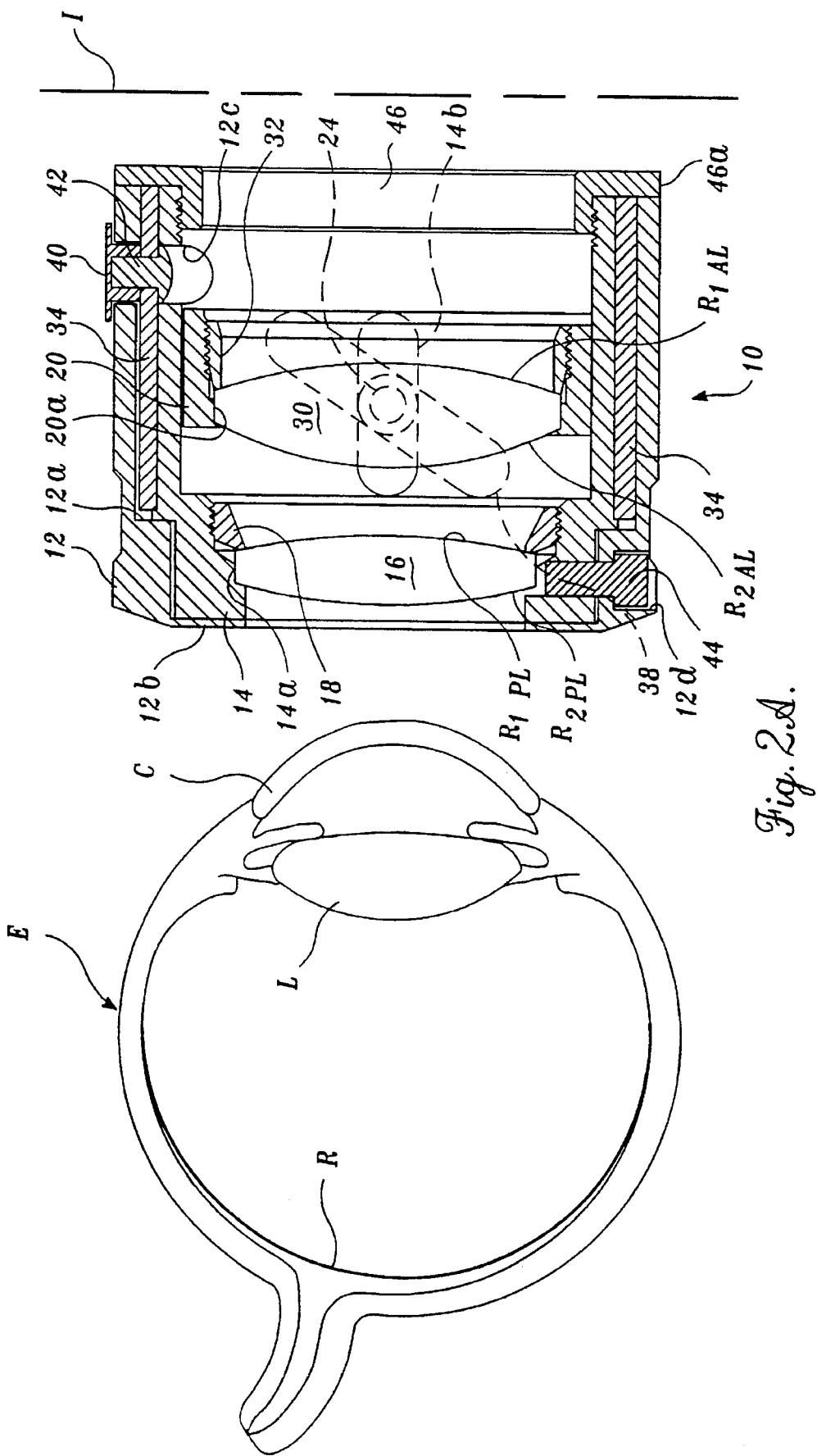
FIGS. 2A, 2B and 2C are longitudinal cross-sectional views of the lens in accordance with the present invention positioned in juxtaposition to the eye showing the anterior lens movable relative to the posterior lens.

Referring first to FIGS. 1 and 2A, the indirect ophthalmoscopy lens 10 of the present invention is enclosed in a housing 12. The housing is annular and has adjacent its posterior end an internal, anterior facing shoulder 12a. The shoulder 12a is formed by a reduced diameter portion of the housing having a slightly lesser diameter than the main portion. An annular flange 12b extends radially inwardly from the posterior end of the reduced diameter portion. The interior diameter of the annular flange 12b is preferably on the order of or slightly larger than the diameter of the cornea C of the eye E.

A posterior lens carrier 14 is also annularly shaped and carries at its posterior end an internal lens receiving groove 14a. The posterior lens carrier 14 is internally threaded anterior to the groove 14a to receive an exteriorly threaded, posterior lens locking ring 18. The posterior lens 16 is positioned in the groove 14a and the locking ring 18 is threaded onto the interior threads in the posterior lens carrier 14 to hold the lens in place. The posterior lens carrier 14 is positioned within the housing 12 and affixed thereto in nonrotating relationship by a set screw 44. The set screw is threaded through a bore 12d in the reduced diameter portion of the housing 12. The set screw engages the exterior portion in the posterior lens carrier 14 to lock it in place.

The anterior lens carrier 20 is sized to telescopically slide within the portion of the posterior lens carrier 14 anterior to the posterior lens 16. The anterior lens carrier 20 has a lens receiving groove 20a in which the anterior lens 30 is positioned. An anterior lens locking ring 32 engages internal threads in the anterior portion of the anterior lens carrier 20 to secure the anterior lens 30 in place. Thus the anterior lens 30 is mounted coaxially with and in telescoping relationship to the posterior lens 16.

The posterior lens carrier 14 has a pair of longitudinal slots 14b positioned 180° from each other. The longitudinal slots 14b that run from a position adjacent the posterior lens locking ring 18 toward the anterior edge of the posterior lens carrier 14. The anterior lens carrier ring 20 has a pair of diametrically opposed bores 26 on its exterior surface that receive outwardly projecting guide pins 22 and 24. Guide pins 22 and 24 ride in the longitudinal slots 14b in the posterior lens carrier 14. The guide pins 22 and 24 allow the anterior lens carrier ring 20 to translate longitudinally, but prevent it from rotating. Thus, the anterior lens 30 can move longitudinally relative to and along the common optical axis with the posterior lens 16.

The outer diameter of the posterior lens carrier 14 and the inner diameter of the housing 12 are sized to provide an annular space therebetween. A cam ring 34 is positioned in this annular space for rotating but nontranslating movement relative to both the posterior lens carrier 14 and the housing 12. The housing 12 is provided with a circumferential slot 12c, the center of which is positioned about 90° from the location of the longitudinal slots 14b in the posterior lens carrier 14. A thumb lever 40 rides in the circumferential slot 12c. The lever 40 is fastened to the cam ring 34 by a screw 42. The posterior lens carrier 14 also has a slot 14c corresponding in location to circumferential slot 12c in the housing 12 so that the screw 42 can be threaded from the inside of the carrier 14 into a bore 34a in the bottom of the lever 40. The head of the screw 42 rides in the slot 14c out of the optical path of the lenses.

The cam ring 34 also carries a pair of cam slots 36 and 38. Cam slots 36 and 38 are spiral in shape and are positioned on opposite sides of the cam ring 34. The cam slots 36 and 38 spiral in opposite directions. The guide pins 22 and 24 extend through the longitudinal slots 14b in the posterior lens carrier 14 and engage the sides of the cam slots 36 and 38. As the lever 40 is moved circumferentially along slot 12c, cam ring 34 rotates. As cam ring 34 rotates, the sides of the cam slots exert longitudinal pressure on the guide pins 22 and 24 causing the anterior lens carrier 20 to move longitudinally relative to the housing 12. Thus, as the cam ring 34 is rotated in one direction, the anterior lens 30 is caused to move toward the posterior lens 16. As the cam ring 34 is rotated in the opposite direction, the anterior lens 30 is moved away from the posterior lens 16.

Finally, all of the internal elements of the lens system are held in place by a rear closure ring 46. Closure ring 46 has external threads which engage internal threads adjacent the anterior end of the posterior lens carrier 14. A radially outwardly extending flange 46A extends outwardly to a position adjacent the outer surface of the housing 12, thus serving to lock all components, including the cam ring 34, in place.

Figure 2B:
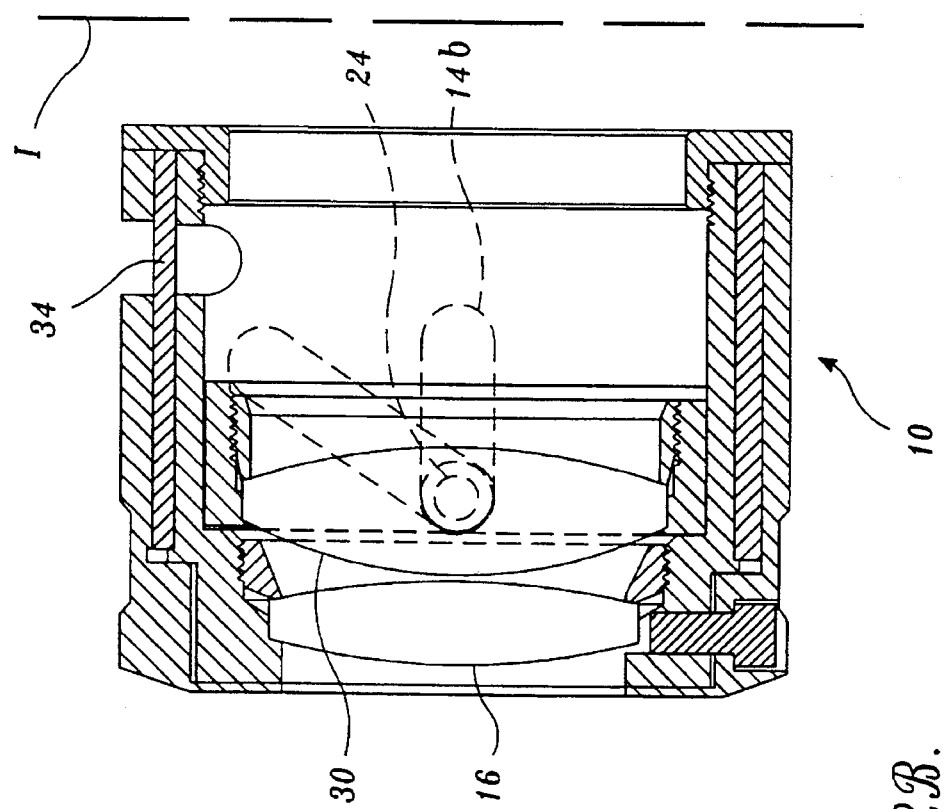
Figure 2B:
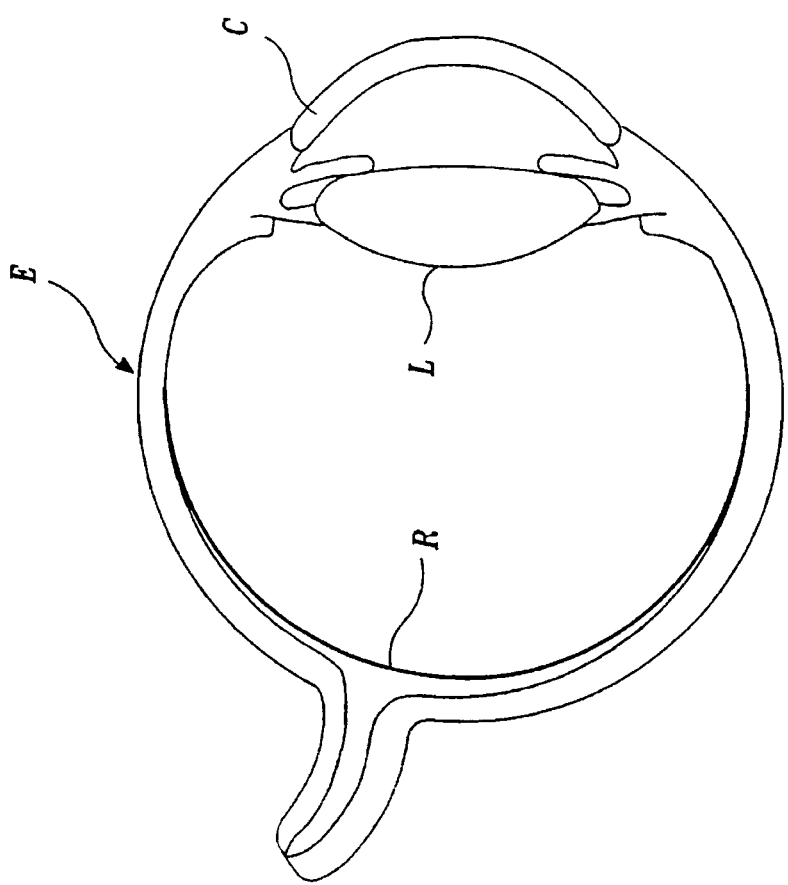
Figure 2C:
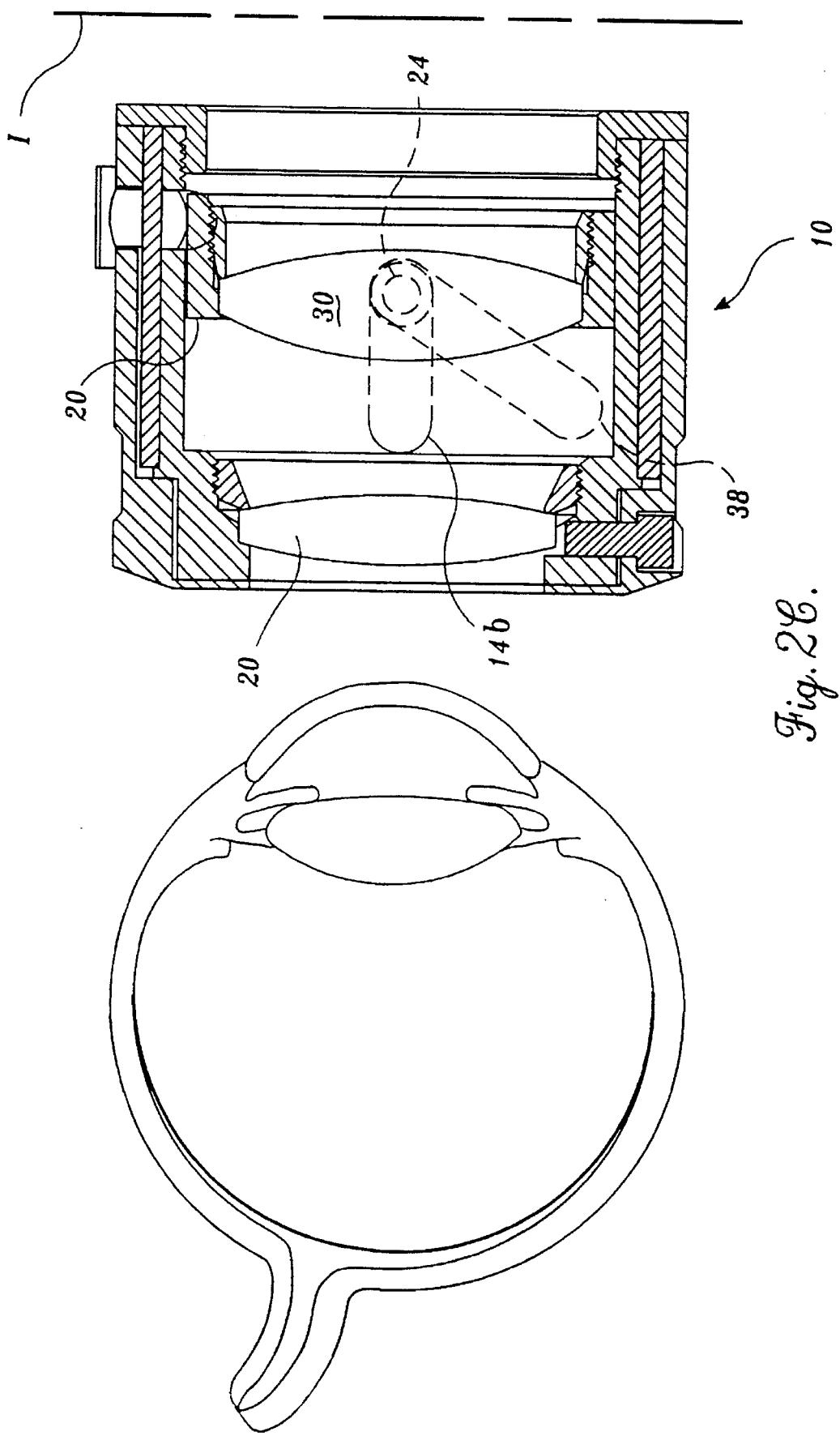

Still referring to FIG. 2A, the anterior lens 30 is shown positioned midway in the longitudinal slot 14b and spiral slot 38. Moving to FIG. 2B, the cam ring 34 has been rotated in a counterclockwise position (from the physician's view point, that is, looking toward the anterior lens 30) so that the guide pin 24 has been moved to the posterior end of the slot 14b, thus positioning the anterior lens 30 in close proximity to the posterior lens 16. In this position, the lenses provide the least magnification, but a wider field of view, of the retina R of the eye E. The image I produced by the lens system is aerial and positioned anterior to, but in proximity to, the anterior end of the lens assembly 10. When the cam ring 34 is rotated in a clockwise direction (again from the physician's viewpoint) the coaction of the cam slots (only 38 is shown) and the guide pins (only 24 is shown) serves to move the guide pin 24 to the anterior end of the longitudinal slot 14b. As this occurs, the anterior lens carrier ring 20 is moved anteriorly to position the anterior lens 30 distally from the posterior lens 16. In this position, the rays from the retina travel through the crystalline lens L, the cornea C through the posterior lens 16 and anterior lens 30 to form an aerial image I that has a lesser field of view but higher magnification than the image I formed when the anterior lens 30 is positioned proximally to the posterior lens 16.

Referring to FIG. 2A, anterior lens 30 has a posterior surface with a radius $R_{2_{AL}}$ and an anterior surface $R_{1_{AL}}$. Similarly, posterior lens has an anterior surface $R_{1_{PL}}$ and a posterior surface $R_{2_{PL}}$. These surfaces can be spherical or aspheric, depending upon the characteristics desired for the adjustable lens. In this embodiment, it is preferred that the anterior lens 30 has two aspheric surfaces while the posterior lens has both spherical surfaces. The aspheric surfaces of the lenses are defined by the formula:

$$Z = \frac{CK^2}{1 + \sqrt{1 - C^2 E K^2}} + A_4 K^4 + A_6 K^6 + A_8 K^8 + \ldots$$

wherein
  $C = (1/R)$,
  $E = b + 1$,
  $K^2 = x^2 + y^2$,
  $A_n$ are higher order aspheric coefficients, and
  wherein Z is in the direction of the optical axis and x and y are orthogonal thereto.

A positive R yields a convex surface and a negative R defines a concave surface. For the preferred embodiment $R_{1_{AL}}$ is 16.74 mm and b is −16.21, and $R_{2_{AL}}$ is 24.78 mm and b is −1.138. The thickness of the anterior lens is 6.70 mm at the optical axis, the diameter is 23.0 mm, and the index of refraction is 1.504. It is preferred that the surfaces of the posterior lens both be spherical, where $R_{1_{PL}}$ is 43.41 mm and $R_{2_{PL}}$ is 39.03 mm. The preferred thickness at the optical axis is 4.5 mm, the preferred diameter is 20.0 mm, and the index of refraction is 1.81. In the preferred embodiment, all $A_n = 0$. These values can vary by up to ±20% without significant deterioration in performance. It is preferred that the values not deviate by more than ±10% and most preferred that they not deviate from ±5%.

In practice, for the preferred embodiment, the working distance from the posterior surface of the posterior lens to the cornea is about 5 mm. The separation between the posterior and anterior lenses can range from 0.5 mm to 7.89 mm. When at 0.5 mm, the lenses provide a combined 77.5D configuration with a magnification of −0.77x and a field of view of 100 degrees. At the 7.89 mm separation, the lenses provide a 64D configuration, with a magnification of −0.94x and a field of view of 78 degrees.

Referring now to FIG. 3, a schematic view of a contact lens employing the concepts of the present invention are disclosed. In this embodiment, the posterior surface of a contact lens 60 is positioned in contact with the cornea C of the eye E. The posterior surface 62 of the contact lens 60 has a curvature that approximates the anterior curvature of the cornea C. The anterior surface 64 of the contact lens 60 also has a predetermined curvature. In this embodiment, two lenses anterior to the contact lens 60 are employed, an anterior lens 66 and an intermediate anterior lens 68. Each of these lenses have posterior and anterior surfaces of predetermined curvature. While this embodiment has two lenses 66 and 68, it can also be designed with a single lens or with more elements than shown. One of ordinary skill after reviewing the foregoing specification will readily be able to construct a cam mechanism which will move one or both of the anterior lens 66 and intermediate anterior lens 68 longitudinally relative to the contact lens 60. Light rays emanating from the retina pass through the crystalline lens L, the cornea C, and are refracted by the contact lens 60, intermediate anterior lens 68, and anterior lens 66 to form an aerial image I" anterior to the anterior lens 66. By manipulating the longitudinal spacing of the intermediate anterior lens 68 and anterior lens 66 in proximity to the contact lens 60, the magnification of the aerial image I" can be modified. In fact, by differentially moving the lenses, the location of the aerial image I" can be maintained at a fixed spacing from the anterior side of the lens combination so that refocusing of the physician's microscope is not required.

The present invention has been described in conjunction with the preferred embodiments and alternates thereto. One of ordinary skill, after reading the specification, will understand that various changes can be made without departing from the broad concepts disclosed therein. For example, two or more lenses can be used in addition to the posterior lens shown in both embodiments herein. Also, the lenses disclosed are designed to be hand-held. One of ordinary skill can easily adapt them to be held by mechanical means such as an articulated arm attached to the examining table, microscope, or other convenient mounting point. Finally, one of ordinary skill will be able to adapt the finger-manipulated lens mounting mechanism to be powered, for example, by a miniaturized electric motor of the type commercially available. It is therefore intended that the scope of protection granted hereon be limited only by the definition contained in the appended claims and equivalents thereof.

The embodiments of the invention in which an exclusive property or privilege is claimed are defined as follows:

1. A lens used in indirect ophthalmoscopy for viewing the fundus of the eye comprising:

a posterior lens having a posterior surface and an anterior surface, the posterior surface having a predetermined curvature and being adapted to be placed in juxtaposition with the cornea, the anterior surface having a predetermined curvature, at least one anterior lens having an anterior surface and a posterior surface, the surfaces of the posterior lens and the surfaces of the anterior lens having curvatures adapted to focus light rays emanating from the fundus when the posterior lens is in juxtaposition to the cornea in an aerial image anterior to and in close proximity to the anterior surface of the anterior lens, and means for coupling said posterior lens and said anterior lens together so that the anterior lens and the posterior lens are substantially coincident along their optical axes, and so that the anterior lens and posterior lens can be moved axially relative to each other between a proximal position and a distal position, the surfaces of the posterior lens and the surfaces of the anterior lens cooperating to change the magnification of the aerial image from at least a first predetermined value when the anterior lens is in a proximal position to a second predetermined value when the anterior lens is in the distal position.

2. The lens of claim 1 wherein said posterior lens is a contact lens, the posterior surface of the contact lens having a curvature approximating that of the cornea and adapted to be placed in contact with the cornea.

3. The lens of claim 1 further comprising a third lens positioned between the posterior lens and the anterior lens, and means coupling the third lens to the posterior lens and the anterior lens for axial movement relative to at least one thereof, said third lens refracting the rays emanating from the fundus of the eye to aid the anterior lens and the posterior lens in changing magnification as said anterior lens is moved relative to said posterior lens.

4. A lens used in ophthalmoscopy for viewing the fundus of the eye comprising:

a contact lens having a posterior surface and an anterior surface, the posterior surface having a curvature corresponding generally to the curvature of the cornea and adapted to be placed in contact with the cornea, the anterior surface having a predetermined curvature, at least one anterior lens having an anterior surface and a posterior surface, the anterior surface of the contact lens and the surfaces of the anterior lens having curvatures adapted to focus light rays emanating from the fundus when the contact lens is in contact with the cornea in an aerial image anterior to and in close proximity to the anterior surface of the anterior lens, and means for coupling said contact lens and said anterior lens together so that the anterior lens and the contact lens are substantially coincident along their optical axes, and so that the anterior lens can be moved axially relative to the contact lens between a position proximal to the contact lens and a position distal from the contact lens, the anterior surface of the contact lens and the surfaces of the anterior lens cooperating to change the magnification of the aerial image from at least a first predetermined value when the anterior lens is in a proximal position to a second predetermined value when the anterior lens is in the distal position.

* * * * *